(12) United States Patent
Farage

(10) Patent No.: US 8,147,466 B2
(45) Date of Patent: Apr. 3, 2012

(54) METHOD OF DETERMINING A SKIN AGENT TRANSFERRED TO SKIN

(75) Inventor: Miranda Aref Farage, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 667 days.

(21) Appl. No.: 12/019,713

(22) Filed: Jan. 25, 2008

(65) Prior Publication Data

US 2009/0192476 A1     Jul. 30, 2009

(51) Int. Cl.
*A61M 35/00*     (2006.01)

(52) U.S. Cl. ........................... 604/290; 382/128

(58) Field of Classification Search ............... 604/19, 604/359, 180, 289–290, 306–308, 317, 358, 604/363–368; 600/306, 345; 602/57–58; 206/440–441; 382/128; 128/849, 853, 854, 128/888; 514/60, 463, 715, 722–724, 738
See application file for complete search history.

(56) References Cited

U.S. PATENT DOCUMENTS

| | | | |
|---|---|---|---|
| 5,160,315 | A | 11/1992 | Heinecke et al. |
| 5,531,855 | A | 7/1996 | Heinecke et al. |
| 6,426,444 | B2 | 7/2002 | Roe et al. |
| 6,515,029 | B1 | 2/2003 | Krzysik et al. |
| 6,937,749 | B2 | 8/2005 | Garnier |
| 7,211,043 | B2 | 5/2007 | Pruche et al. |
| 2003/0069482 | A1 * | 4/2003 | Workman et al. ............. 600/306 |
| 2003/0108228 | A1 * | 6/2003 | Garnier ........................ 382/128 |
| 2007/0118085 | A1 | 5/2007 | Farage |
| 2007/0249055 | A1 * | 10/2007 | Farage ............................ 436/85 |

OTHER PUBLICATIONS

Miranda A. Farage, Sandy Meyer & David Walter, Procter & Gamble Co., Winton Hill Tech Center, Cincinnati, OH, Development of a sensitive test method to evaluate mechanical irritation potential on mucosal skin, Skin Research and Technology 2004; 10:85-95, Printed, Denmark. © Blackwell Munksgaard, 2004, Pub. Sep. 8, 2003.

Miranda A. Farage, Sandy Meyer & David Walter, Procter & Gamble Co., Winton Hill Tech Center, Cincinnati, OH, Evaluation of modifications of the traditional patch test in assessing the chemical irritation potential of feminine hygiene products, Skin Research and Technology 2004; 10:73-84, Printed, Denmark. © Blackwell Munksgaard, 2003, Pub. Sep. 8, 2003.

Miranda A. Farage, Debbie A. Gilpin, Ninah A. Enane & Sue Baldwin, Procter & Gamble Co., Winton Hill Tech Center, Sharon Woods Tech Center & Baby Care Products, Cincinnati, OH, Development of a new test for mechanical irritation: behind the knee as a test site, Skin Research and Technology 2001; 7:193-203, Printed, Denmark. © Munksgaard, 2001, Pub. Aug. 22, 2000.

(Continued)

*Primary Examiner* — Tatyana Zalukaeva
*Assistant Examiner* — Benedict L Hanrahan
(74) *Attorney, Agent, or Firm* — Megan C. Hymore; James E. Oehlenschlager

(57) ABSTRACT

A method of determining an amount of skin agent transferred from an absorbent article to an area of human skin is provided. An absorbent article is applied to and then after use removed from an area of skin. Tape is then releasably attached to and removed from the area of skin. The amount of skin agent that adheres to the tape is then analyzed to determine the amount of skin agent transferred to the area of skin.

18 Claims, 1 Drawing Sheet

OTHER PUBLICATIONS

S. Baldwin, M. R. Odio, S. L. Haines, R. O'Connor, S. Englehart, A. T. Lane, Procter & Gamble Co., Stanford University School of Medicine, Palo Alto, CA, Procter & Gamble Co., 11450 Grooms Road, Cincinnati, OH, Skin benefits from continuous topical administration of a zinc oxide/petrolatum formulation by a novel disposable diaper, JEADV (2001) 15(Suppl. 1)5-11, © 2001 European Academy of Dermatology and Venereology.

Mauricio R. Odio, Robert J. O'Connor, Frank Sarbaugh, & Sue Baldwin, Procter & Gamble Co., Cincinnati, OH, Continuous Topical Administration of a Petrolatum Formulation by a Novel Disposable Diaper, Pharmacology and Treatment, Dermatology 2000; 200-238-243, © 2000 S. Karger AG, Basel.

Mauricio R. Odio, Robert J. O'Connor, Frank Sarbaugh, & Sue Baldwin, Procter & Gamble Co., Cincinnati, OH, Continuous Topical Administration of a Petrolatum Formulation by a Novel Disposable Diaper, Pharmacology and Treatment, Dermatology 2000; 200-232-237, © 2000 S. Karger AG, Basel.

PCT Search Report, International App. No. PCT/IB2009/050249, mail date Jun. 22, 2010, 14 pages.

* cited by examiner

METHOD OF DETERMINING A SKIN AGENT TRANSFERRED TO SKIN

FIELD OF THE INVENTION

The present invention relates to methods for determining the amount of a skin agent transferred from an absorbent article to human skin.

BACKGROUND OF THE INVENTION

Absorbent articles may include various skin agents. Skin agents can be used either to treat a negative condition, such as skin trauma, or to provide a beneficial effect, such as a pleasing odor. Absorbent articles, for example diapers and feminine hygiene pads are normally in close and sustained contact with an area of skin. Further, absorbent articles are often used on areas of the skin where there is frequent motion. Due to the friction produced by the frequent motion, the area of skin to which the absorbent article is applied may develop either clinical or subclinical symptoms of irritation. Additionally, these areas of the skin are generally moist, providing an environment that promotes the growth of microorganisms, such as bacteria. The bacteria can irritate an area of skin or cause an infection. A variety of skin agents have been added to absorbent articles to lower friction and soothe skin irritation. Additionally, absorbent articles have included other skin agents, such as vitamins or anti-bacterial treatments to provide beneficial effects to users.

The desirability of adding skin agents to absorbent articles has been recognized, however there remains the challenge of determining the amount of a skin agent that transfers to an area of skin. The determination of the amount of skin agent transferred could be used to determine what amounts provide either a positive or a negative effect to a user.

One method uses tape to determine the amount of a skin agent transferred from an absorbent article to an area of skin. The adhesive layer of the tape is placed on an area of skin, after which an absorbent article is positioned over the tape. During the wear time of the absorbent article, skin agent is transferred to the tape surface facing the absorbent article. Following removal of the absorbent article the tape is peeled off the area of skin, and analyzed to determine the amount of skin agent transferred to the tape surface. There are several problems with this method. For example, the tape generally has a smooth surface compared to the irregular surface of skin. As a result, the smooth surface of the tape has a comparatively smaller surface area than an equally sized area of skin. Thus, the tape would be exposed to less skin agent than an equally sized area of human skin, due to the reduction in surface area. In addition, the smooth surface of the tape may allow the skin agent transferred to the tape to be transferred back to the absorbent article or removed there from, by movement of the absorbent article across the surface of the tape. Further, exudates, such as blood, menstrual fluid, urine, sebum (oils) and sweat that can be present on or in an area of skin may affect skin agent transfer, and are not present on a tape.

As such it would be desirable to provide a method for determining the amount of a skin agent that is transferred from an absorbent article to an area of skin.

SUMMARY OF THE INVENTION

A method for determining an amount of a skin agent transferred from an absorbent article to an area of skin is provided. The method comprises the steps of providing an absorbent article including a skin agent, applying the absorbent article to an area of skin, and removing the absorbent article from the area of skin. After removal of the absorbent article a tape is provided that comprises an adhesive layer and a backing material. The adhesive layer of the tape is releasably attached to the area of skin from which the absorbent article was removed, after which the tape is removed. The amount of skin agent present on the tape is then determined.

A method for determining an amount of a skin agent transferred from an absorbent article to an area of skin is provided. The method comprises the steps of providing an absorbent article including a skin agent, applying the absorbent article to an area of skin, wherein the area of skin is at least one of axilla, popliteal fossa, urogenital area, talus, buccala, auris auricula, palpebra, buccocervical, digitus web, crapus or cubitus, and removing the absorbent article from the area of skin. After removal of the absorbent article a tape is provided that comprises an adhesive layer and a backing material. The adhesive layer of the tape is releasably attached to the area of skin from which the absorbent article was removed, after which the tape is removed. The amount of skin agent present on the tape is then determined.

DETAILED DESCRIPTION OF THE INVENTION

Figure 1:
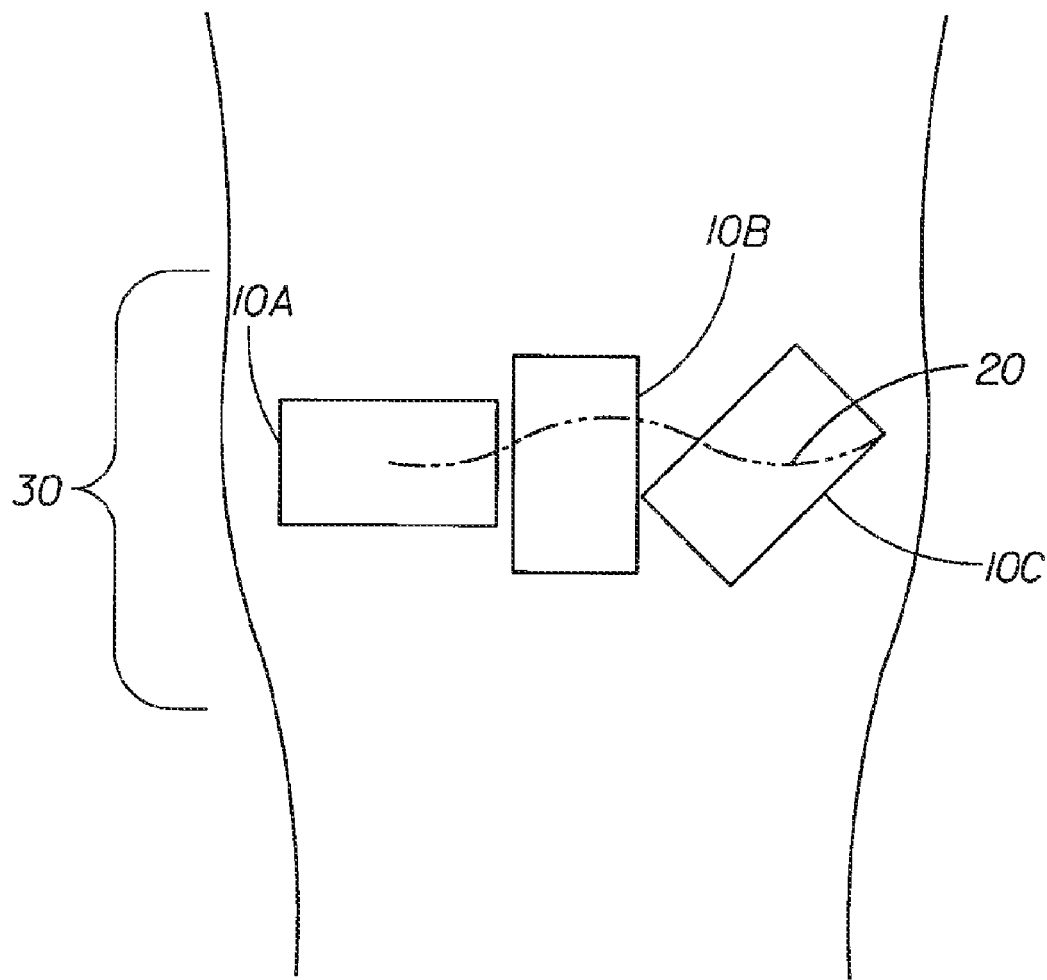
FIG. 1 shows absorbent articles applied horizontally, vertically, or diagonally in relation to the crease in the area behind the knee (popliteal fossa).

It has been discovered that the amount of a skin agent transferred from an absorbent article, such as a feminine hygiene pad or diaper, to an area of human skin, can be determined using the new method described herein. The present invention provides for the collection of a wide variety of data concerning the transfer of a skin agent from an absorbent article to an area of skin. The method as described herein can be used to consistently determine the amount of a skin agent transferred from an absorbent article to an area of skin. The data collected using the method leads to consistent and objective determinations of the ability of various absorbent articles to transfer skin agents to an area of skin. The capability to determine the amount of a skin agent transferred to, and possibly absorbed by, an area of skin can be used to evaluate the overall safety, and effectiveness of an absorbent article. Additionally, this type of data may be useful in the development of improved absorbent articles.

The present invention can be used to determine if bodily substances, such as, for example, blood, menstrual fluid, urine, sebum or, sweat when present on or in an area of skin, affect the transfer of a skin agent from an absorbent article to an area of skin. Additionally, the present invention can be used to determine if skin agents, when present on an area of skin, will positively or negatively affect the transfer of other skin agents from an absorbent article to the area of skin. Further, the present invention can be used to determine the amount of skin agent present on or in an area of skin after the removal of the absorbent article, for example, to determine how long a skin agent remains on an area of skin after removal of the absorbent article. Additionally, the present invention can be used to determine the effect, if any, upon a skin agent, produced by treatment of the area of skin after removal of the absorbent article. Such treatment can include washing, wiping, or scrubbing the area of skin.

As used herein "area of skin" refers to an area of skin on a human body that may have absorbent articles applied thereto.

The area of skin may be any suitable size for the application of an absorbent article. In certain embodiments, the area of skin may have a size of about 5 cm×about 5 cm. The area of skin may have any suitable surface contour, such as planar, rounded or irregular. The area of skin may have hair or no hair. For example, the area of skin may be shaved or unshaved. The area of skin, in certain embodiments, may be keratinized (normal) skin, vulvar or mucosal skin. The absorbent article is applied to an area of skin that is capable of stretching and contracting during normal movement, such as walking. Examples include the under arm area (axilla), area behind the knee (popliteal fossa), urogenital area, ankle area (talus), area under the chin (buccala), ear area (auris auricula), eyelids (palpebra), neck area (buccocervical), finger webs (digitus web), wrist area (crapus) or elbow area (cubitus). In certain embodiments, the stretching and contracting of an area of skin against the surface of an absorbent article may cause friction leading to trauma, such as irritation or tenderness. The trauma may compromise the barrier function of the outermost layer of the skin, the stratum corneum, allowing a skin agent to be absorbed by deeper layers of the skin, such as stratum lucidum or stratum granulosum or even to enter the blood stream (i.e. the amount of skin agent transferred to an area of skin is increased when there is friction at the area of skin).

As used herein "predetermined period of time" refers to the amount of time an absorbent article may be applied to an area of skin. The absorbent article may be applied to an area of skin for a period of time that corresponds to that absorbent article's typical application time during normal use. For example, feminine hygiene pads could be applied about every three hours, to correspond with the typical application time of feminine hygiene pads. In certain other embodiments, an absorbent article may be applied to an area of skin for an extended period of time as compared to a typical application period of time to determine what effects if any there are on the area of skin. In certain other embodiments, an absorbent article may be applied to an area of skin for a shorter period of time as compared to a typical application period of time.

As used herein "predetermined length of time" refers to the amount of time a tape is releasably attached to an area of skin. In certain embodiments, the length of time a tape is releasably attached to an area of skin may depend on factors, such as the size of the tape, the amount of pressure used to releasably attach the tape, the skin agent (amount in absorbent article, known or estimated skin absorbency), number of tapes releasably attached to an area of skin, area of skin (presence of hair, location on body, thickness of skin) and/or any other factors known in the art. In certain embodiments, the length of time a tape is releasably attached to an area of skin may be about one hour or less, and in certain other embodiments, the length of time a tape is releasably attached to an area of skin may be about half an hour or less. In still further embodiments, a tape may be removed immediately or soon after it is releasably attached to an area of skin.

"Skin agent" as used herein refers to a biological or chemical composition that may be part of, present in, or on the surface of an absorbent article. Skin agents may be transferable from an absorbent article to an area of skin. Examples of skin agents include at least one of the following: emollients, immobilizing agents, nanotechnology agents, encapsulated time release agents, skin healants, anesthetics, analgesics, perfumes, such as long lasting or enduring perfumes, antibacterial agents, antiviral agents, botanical agents, disinfectants, pharmaceutical agents, film formers, dyes, inks, colorants, surfactants, absorbents, wet strength agents, deodorants, opacifiers, astringents, solvents, biological agents, such as bacteria, viruses and their toxins, absorbent article materials or mixtures thereof.

"Lotions" may comprise one or more skin agents, such as emollients and immobilizing agents. Lotions may be in the form of emulsions or dispersions. Lotions may be shear thinning or they may strongly change their viscosity around skin temperature to allow for transfer and easy spreading on an area of skin. Lotions may be semi-solid or of high viscosity so they do not substantially flow without activation during the life of the product or gel structures. Lotions may sooth, moisturize, and/or lubricate the area of skin.

"Emollients" as used herein, refers to materials that soften, soothe, supple, coat, lubricate, moisturize, or cleanse an area of skin and may include at least one of glycols (such as propylene glycol and/or glycerine), polyglycols (such as triethylene glycol), petroleum-based materials, fatty acids, fatty alcohols, fatty alcohol ethoxylates, fatty alcohol esters and fatty alcohol ethers, fatty acid ethoxylates, fatty acid amides and fatty acid esters, alkyl ethoxylates, oils, squalane, fluorinated emollients, silicones, siloxanes, organosilicones, quaternary ammonium compounds, ester-functional quaternary ammonium compounds, or mixtures thereof. In certain embodiments, an emollient will reduce the surface friction of the surface of an absorbent article compared to a surface of an absorbent article without such an emollient. An emollient may or may not be transferable. In certain embodiments, an emollient may be substantially non-transferable.

Petroleum-based materials include 16 to 32 carbon atom hydrocarbons, or mixtures of 16 to 32 carbon atom hydrocarbons. Petroleum based hydrocarbons having these chain lengths include petrolatum (also known as "mineral wax," "petroleum jelly" and "mineral jelly"). Petrolatum usually refers to more viscous mixtures of hydrocarbons having from 16 to 32 carbon atoms. A Petrolatum that may be used is available from Witco, Corp., Greenwich, Conn. as White Protopet® 1 S.

Fatty acid esters that may be used include but are not limited to those derived from long chain $C_{12}$-$C_{28}$ fatty acids, such as $C_{16}$-$C_{22}$ saturated fatty acids, and short chain $C_1$-$C_8$ monohydric alcohols, such as $C_1$-$C_3$ monohydric alcohols. Nonlimiting examples of fatty acid ester emollients include but are not limited to at least one of methyl palmitate, methyl stearate, isopropyl laurate, isopropyl myristate, isopropyl palmitate, ethylhexyl palmitate, or mixtures thereof. Fatty acid ester emollients can also be derived from esters of longer chain fatty alcohols (such as $C_{12}$-$C_{28}$, $C_{12}$-$C_{16}$) and shorter chain fatty acids e.g., lactic acid, such as lauryl lactate and cetyl lactate.

Alkyl ethoxylates may include but are not limited to at least one of $C_{12}$-$C_{18}$ fatty alcohol ethoxylates having an average of from 3 to 30 oxyethylene units, such as from about 4 to about 23. Nonlimiting examples of such alkyl ethoxylates include laureth-3 (a lauryl ethoxylate having an average of 3 oxyethylene units), laureth-23 (a lauryl ethoxylate having an average of 23 oxyethylene units), ceteth-10 (acetyl ethoxylate having an average of 10 oxyethylene units), steareth-2 (a stearyl ethoxylate having an average of 2 oxyethylene units), steareth-10 (a stearyl ethoxylate having an average of 10 oxyethylene units) or mixtures thereof. These alkyl ethoxylate emollients may be used in combination with the petroleum-based emollients, such as petrolatum, at a weight ratio of alkyl ethoxylate emollient to petroleum-based emollient of from about 1:1 to about 1:3. In certain embodiments, from about 1:1.5 to about 1:2.5.

"Oils" that may be used in the present invention include, but are not limited to mineral oil, silicone oil, silicone gels or mixtures thereof. Silicones include but are not limited to at least one of polydimethylsiloxanes, aminosilicones, cationic silicones, quaternary silicones, silicone betaines or mixtures thereof. In certain embodiments, the siloxane may be an aminofunctional polydimethylsiloxane, such as aminoethylaminopropyl polydimethylsiloxane.

"Quaternary ammonium compounds" that may be used in the present invention include, but are not limited to dialkyldimethylammonium salts, such as ditallowedimethylammonium chloride, ditallowedimethylammonium methylsulfate, di(hydrogenated tallow)dimethylammonium chloride or mixtures thereof. In one example, the emollient comprises di(hydrogenated tallow)dimethylammonium chloride, commercially available from Witco Chemical Company Inc. of Dublin, Ohio as Varisoft 137®.

"Ester-functional quaternary ammonium compounds" that may be used in the present invention include, but are not limited to diester dialkyl dimethyl ammonium salts, such as diester ditallow dimethyl ammonium chloride, monoester ditallow dimethyl ammonium chloride, diester ditallow dimethyl ammonium methyl sulfate, diester di(hydrogenated) tallow dimethyl ammonium methyl sulfate, diester di(hydrogenated)tallow dimethyl ammonium chloride, or mixtures thereof. In one embodiment, the emollient comprises diester ditallow dimethyl ammonium chloride and/or diester di(hydrogenated)tallow dimethyl ammonium chloride, both commercially available from Witco Chemical Company Inc. of Dublin, Ohio under the tradename "ADOGEN SDMC™."

Lotions may include an "immobilizing agent," which acts to prevent migration of the emollient so that it can remain primarily on the surface of the absorbent article to which it is applied. This allows the emollient to deliver maximum softening benefit, as well as be available for transfer to an area of skin. Immobilizing agents may function as viscosity increasing agents and/or gelling agents. Immobilizing agents may include but are not limited to waxes, such as ceresin wax, ozokerite, microcrystalline wax, petroleum waxes, fisher tropsh waxes, silicone waxes, paraffin waxes, polyethylene waxes, beeswax, fatty alcohols, such as cetyl, cetaryl, cetearyl and/or stearyl alcohol, fatty acids and their salts, such as metal salts of stearic acid, mono and polyhydroxy fatty acid esters, mono and polyhydroxy fatty acid amides, silica and silica derivatives, gelling agents, thickeners or mixtures thereof.

"Nanotechnology agents" are organic or inorganic nanotechnology agents having average diameters of about 500 micrometers (μm) or less. In certain embodiments, nanotechnology agents may have average diameters of from about 2 μm to less than about 500 μm, from about 2 μm to less than about 100 μm, and from about 2 μm to less than about 50 μm. In certain embodiments, nanotechnology agents can also include crystalline or amorphous materials.

"Inorganic nanotechnology agents" may include oxides, such as inorganic metal oxides, silicates, such as layered clay minerals, carbonates and hydroxides. "Inorganic metal oxides" may be natural or synthetic and generally fall within two groups: photoactive and non-photoactive nanotechnology agents. General examples of photoactive metal oxide nanotechnology agents include zinc oxide and titanium oxide. Photoactive metal oxide nanotechnology agents require photoactivation from either visible light (e.g. zinc oxide) or from UV light (e.g. titanium oxide). Zinc oxide coatings have generally been used as anti-microbial agents or as anti-fouling agents.

"Non-photoactive metal oxide nanotechnology agents" do not use UV or visible light to produce the desired effects. Examples of non-photoactive metal oxide nanotechnology agents include, but are not limited to silica and alumina nanotechnology agents, and mixed metal oxide nanotechnology agents including, but not limited to saponites, and hydrotalcite.

"Layered clay minerals" may be either naturally occurring or synthetic and include those in the geological classes of smectites, kaolins, illites, chlorites, attapulgites and mixed layer clays. Smectites, include montmorillonite, bentonite, pyrophyllite, hectorite, saponite, sauconite, nontronite, talc, beidellite, volchonskoite and vermiculite. Kaolins include kaolinite, dickite, nacrite, antigorite, anauxite, halloysite, indellite and chrysotile. Illites include bravaisite, muscovite, paragonite, phlogopite and biotite. Chlorites include corrensite, penninite, donbassite, sudoite, pennine and clinochlore. Attapulgites include sepiolite and polygorskyte. Mixed layer clays include allevardite and vermiculitebiotite.

One or more "skin healants" may be used. Skin healants include but are not limited to at least one of vitamins, such as Vitamin B3, Vitamin E, sucrose esters of fatty acids, anti-inflammatory compounds, lipids, inorganic anions, inorganic cations, protease inhibitors, sequestration agents, alpha bisalbolol, or mixtures thereof.

As used herein, the term "botanical agents" refers to the chemically active components of various plants and plant substances. Botanical agents can include any water-soluble or oil-soluble chemically active component extracted from a particular plant. Examples of botanical agents include extracts from echinacea, yucca glauca, willow herb, basil leaves, aloe, oregano, carrot root, grapefruit fruit, fennel, rosemary, thyme, blueberry, bell pepper, blackberry, blackcurrant fruit, tea leaves, coffee seed, dandelion root, date palm fruit, gingko leaf, hawthorn berries, licorice, sage, strawberry, sweet pea, tomato, vanilla fruit, absinthe, arnica, centella asiatica, chamomile, comfrey, cornflower, horse chestnut, ivy (*Herdera helix*), magnolia, mimosa, oat extract, pansey, skullcap, seabuckthorn, white nettle, witch hazel and any combinations thereof.

As used herein, the term "pharmaceutical agents" refers to drugs for treating injuries, infections, and diseases locally or systemically. Examples of pharmaceutical agents include any material used to improve general health or local skin or mucous tissue conditions, for example therapeutic drugs, such as organic and macromolecular compounds, which in certain embodiments may be polypeptides; proteins; amino acids; and nucleic acid materials comprising DNA (deoxyribose nucleic acid) or RNA (ribonucleic acid).

"Absorbent article" as used herein refers to an article including at least one skin agent, and which comprises one or more natural fibers, synthetic fibers, foams, such as, for example, those formed from High Internal Phase Emulsions (HIPE) or combinations thereof. The absorbent article may be embossed, pattern-densified, creped, uncreped, or include combinations thereof. The absorbent article may also comprise a nonwoven web, cellulosic fiber containing web or combinations thereof. Examples of types of absorbent articles include tampons, feminine hygiene pads, interlabial pads, pantiliners, topsheets, diapers, training pants, adult incontinence products, sanitary tissues, facial tissues, toilet tissues, paper towels, wipes, such as cleaning wipes and dusting wipes, textiles, fabrics, cotton balls, swabs or pads, or wound dressings.

As used herein "absorbent article materials" refers to materials that are used to produce, result from the production of, or form at least a part of an absorbent article. For example, polymers or monomers used to produce foam for an absorbent article may be absorbent article materials. Absorbent article materials may be also include unreacted monomers, intermediates, or processing aids used in the production of an absorbent article, for example, emulsifiers, initiators, or monomers for HIPE foam production, such as EHA (2-ethylhexyl acrylate), EGDMA (ethyleneglycol dimethacrylate), and EHMA (2-ethylhexyl methacrylate).

"Tape" as used herein refers to a removable tape comprising a backing material having an adhesive layer on at least one major surface thereof. The tape should be capable of adhering to an area of human skin, and of being removed therefrom. TEGADERM™HP from 3M™, St. Paul, Minn.; SEB-UTAPE® and D-SQUAME® from CuDerm Corp., Dallas, Tex.; are examples of tape that can be used in the present invention.

The adhesive layer should have sufficient adhesive holding power for adherence to an area of human skin. In certain embodiments, the adhesive holding power of the adhesive layer is less than its cohesive strength, such that the adhesive layer will not separate from the backing material when the backing material is subjected to stress. Examples of stress subjected to the backing material include stress caused by stretching or peeling. A tape can adhere to an area of skin, and can then be removed by simply peeling the tape at an angle from the surface of an area of skin. The tape may be conformable to anatomical surfaces, such that when the tape is releasably attached to an area of skin it conforms to the area of skin, even when the area of skin is moved. For example, when a joint such as a knee is flexed and then returned to its unflexed position, the tape can flex to accommodate the flexion of the joint, but can be resilient enough to continue to conform to the joint when the joint is returned to its unflexed condition.

The adhesive layer may comprise any adhesive suitable for adherence to human skin, such as tackified rubber adhesives, for example natural rubber, olefins, silicones, polyisoprene, polybutadiene, polyurethanes, styrene-isoprene-styrene and styrene-butadiene-styrene block copolymers, and other elastomers; and tackified or untackified acrylic adhesives, such as copolymers of isooctylacrylate and acrylic acid, acrylate copolymers, such as iso-octyl acrylate:acrylamide copolymer, iso-octyl acrylate:n-vinyl pyrrolidone copolymer, crosslinked acrylates and mixtures thereof. The thickness of the adhesive layer, in certain embodiments, can range from about 25 µm to about 1,000 µm, and in certain other embodiments, from about 50 µm to about 400 µm.

The backing material can be in the form of nonwoven fibrous webs, woven fibrous webs, knits, paper, or films, such as single or multi-layer films, porous films, foam-like films, and combinations thereof. The backing material may also be prepared from filled materials, for example filled films, such as calcium carbonate filled polyolefins. In certain embodiments, the backing material may be selected from polyolefins, such as polyethylene, including high density polyethylene, low density polyethylene, chlorinated polyethylene, polypropylene, and polybutylenes; vinyl copolymers, such as polyvinyl chlorides, both plasticized and unplasticized, and polyvinyl acetates; olefinic copolymers, such as ethylene/methacrylate copolymers, ethylene/vinyl acetate copolymers, acrylonitrile-butadiene-styrene copolymers, and ethylene/propylene copolymers; acrylic polymers and copolymers; polyether block amides; and combinations thereof. Mixtures or blends of any plastic or plastic and elastomeric materials, such as polypropylene/polyethylene, polyurethane/polyolefin, polyurethane/polycarbonate, polyurethane/polyester, can also be used.

If the backing material is formed from film, it can be made by any known method of film forming, such as, for example, extrusion, co-extrusion, solvent casting, foaming, non-woven technology, and the like. The backing material can have any thickness, with certain embodiments having thicknesses ranging from about 10 µm to 250 µm.

The tape can be produced by any conventional method for preparing tape. For example, either the adhesive can be directly coated onto the backing material, or it can be formed as a separate layer and then later laminated to the backing material.

In accordance with the present invention, the determination of the transfer of skin agent from an absorbent article to an area of skin is initiated by applying an absorbent article to an area of skin. In certain embodiments, more than one absorbent article may be applied to the same area of skin. An absorbent article may be applied in any suitable direction on an area of skin, and if more than one absorbent article is applied, they may be applied in similar or different directions. For example, an absorbent article 10A, 10B, 10C may be applied horizontally 10A, vertically 10B, or diagonally 10C in relation to the crease 20 in the area behind the knee (popliteal fossa) 30, as shown in FIG. 1. In certain embodiments, before an absorbent article is applied to an area of skin a baseline determination may be attained, by releasably attaching at least one tape to an area of skin. The baseline determination may be used to ascertain if skin agents are already present on an area of skin. In certain other embodiments, an area of skin may be washed prior to application of the absorbent article. For instance, in certain embodiments, the area of skin may be washed with a cleaning solution, such as water, a water and soap mixture, or alcohol. To clean the area of skin, a cleaning implement, such as paper towels, wipes, textiles, fabrics, cotton balls or swabs may be rubbed across the area of skin in a back and forth manner, a circular manner, multi-directional manner, unidirectional manner or combinations thereof.

The absorbent article can be of any suitable size or shape, as determined by the area of skin to which it will be applied. In certain embodiments, the absorbent article that is applied to an area of skin may be a portion of an absorbent article, such as a topsheet or absorbent core of a feminine hygiene pad. In certain other embodiments, after an absorbent article is applied to an area of skin, a means of support may be used to secure the absorbent article to an area of skin. As used herein "means of support" refers to any device or material that is suitable for securing or holding an absorbent article to an area of skin, such as, for example, rolled gauze, bandages, or elastic bands, such as an elastic knee band manufactured by Ace® Brand Knee Braces, Franklin Lakes, N.J. For example, rather than being worn in a typical manner (in the vulvar area), a feminine hygiene pad may be secured to the area of skin behind the knee (popliteal fossa) by an elastic knee band.

After a predetermined amount of time, the absorbent article is removed from an area of skin. The absorbent article may be removed from an area of skin using any suitable means, such as hands or forceps. Additionally, if there are multiple absorbent articles applied to one or more areas of skin they do not all have to be removed at the same time. For example, in certain embodiments, all of the applied absorbent articles do not need to be removed from an area of skin at the same time, as some of the absorbent articles may be left applied to the area of skin while others are removed or even new absorbent articles applied.

Following the removal of an absorbent article from an area of skin, the adhesive layer of a tape may be releasably attached to the area of skin from which the absorbent article had been removed. Factors that determine the number of tapes releasably attached to an area of skin can be: type of skin agent, concentration of skin agent in absorbent article, type of absorbent article, visual inspection of the area of skin, location of area of skin, temperature, time of day, intensity and duration of applied pressure, sex, age, skin type, type of tape, or combinations thereof. One or more tapes may be releasably attached to the same area of skin, for example the area of skin behind the right knee (right popliteal fossa). In certain embodiments, the total number of tapes releasably attached to an area of skin is from about 1 to about 50, in certain other embodiments, the total number of tapes releasably attached to an area of skin is from about 1 to about 20, and in still other embodiments the total number of tapes releasably attached to an area of skin is from about 1 to about 5. A tape may be releasably attached in any suitable direction on an area of skin, and if more than one tape is releasably attached, they may be releasably attached in similar or different directions. A tape may be releasably attached to an area of skin by any suitable means to avoid contamination of the tape, such as using gloved fingers or forceps. Once a tape is releasably attached to an area of skin, pressure may be used to help the tape adhere to the area of skin. In certain embodiments, the amount of pressure applied to the backing material of the tape is from about 0.1 psi (pounds per square inch) to about 3 psi, and in certain other embodiments, the amount of pressure applied to the backing material of the tape is from about 0.5 psi to about 2 psi. In certain embodiments, a finger or any suitable device, such as a roller, flat headed probe, blotter or pressure applying device for example, the D-SQUAME PRESSURE DEVICE, catalogue no. D500 from CuDerm Corp., Dallas, Tex., may be used to apply the pressure.

The tape used may be of any suitable shape, size or type, for releasable attachment to an area of skin. The tape may have any suitable shape for releasable attachment to an area of skin, such as square, rectangular, oval, circular or any other desired shape. In certain embodiments, a tape's outer dimension may be less than the absorbent article's surface area that was applied to the area of skin. In certain embodiments, a tape may be rectangular with outer dimensions of about 6 cm×about 4 cm. In certain other embodiments, the tape may be square with outer dimensions of about 4 cm×about 4 cm. In certain embodiments, anyone or more of the following, such as the shape, size or type of the tape may be determined by factors, such as the area of skin the tape will be releasably attached to, length of time an absorbent article is applied to an area of skin, analytical sensitivity to the skin agent, the absorbent article or the type of skin agent being determined. For example, if the absorbent article has only minute quantities of a skin agent or it is known or estimated that the skin agent will not transfer well to an area of skin, a larger piece of tape may be used (to collect more of the skin agent) as compared to a tape that is used to collect a skin agent that is present in the absorbent article in greater amounts, or is known or estimated to easily transfer to the area of skin.

After a predetermined length of time the tape may be removed from an area of skin. The adhesive properties of the adhesive layer of a tape may be such that removal from the area of skin occurs easily, and without significant discomfort. When a tape is removed from an area of skin, skin agent adheres to the adhesive layer of the tape. In addition, a portion of the outermost layer of the area of skin, such as the stratum corneum, may adhere to the adhesive layer of the tape. The determination of the amount of skin agent transferred to an area of skin has increased accuracy due to the adherence of the outermost layer of skin to the adhesive layer, as the outermost layer of skin may have absorbed skin agent. The accuracy is increased, as in addition to the skin agent present on the surface of an area of skin, skin agent that may have been absorbed by the outermost layer of skin is also removed with the tape. In certain embodiments, when the tape is removed it may be stored in a container, such as a glass sample container available from VWR Scientific, West Chester, Pa. More than one tape may be stored in a single container. In certain embodiments, where only the amount of skin agent absorbed by an area of skin (usually the stratum corneum) was to be determined the initial tapes releasably attached to an area were not analyzed. In certain embodiments, the number of tapes not analyzed was from about 1 to about 10. In certain other embodiments, the number of tapes not analyzed was from about 2 to about 5. In still further embodiments, the number of tapes not analyzed was from about 2 to about 3. The factors that may be used to decide the number of tapes not analyzed can be visual inspection of the area of skin to detect any non-absorbed skin agent on the surface of the area of skin; type of skin agent; type of tape; location of the area of skin; or combinations thereof.

The amount of skin agent transferred to the area of skin may be influenced by factors, such as the location of the area of skin (presence of hair, area of skin thickness, keratinization of the area of skin i.e., palms or soles will be different from vulvar or back areas), presence of any other substances on the surface of the area of skin, such as sebum that may act as barriers to transfer, or the oil/water partition coefficient property of the skin agent (i.e., hydrophobic agents tend to be transferred to an area of skin more readily than hydrophilic agents), or the molecular weight of the skin agent (i.e., smaller molecular weight ingredients tend to be transferred to an area of skin more readily than high molecular weight agents).

In certain embodiments, to help ensure that successive releasable attachments of tape are being releasably attached to the same position on an area of skin, the outer dimensions of the first tape releasably attached to the area of skin may be at least partially marked on the area of skin by using a suitable marking instrument, such as a felt tip marker. After removal of the first tape the marks are left on the area of skin, so that subsequent tape may be releasably attached to the same position on the area of skin as the first tape.

After a tape has been removed, the amount of skin agent adhering thereon is determined using known analytical methods. The amount of skin agent may be expressed in mass per unit area, for example $mg/cm^2$. Therefore, to determine the total amount of skin agent transferred to an area of skin, the mass per unit area is multiplied by the absorbent article's surface area that was applied to the area of skin. One of ordinary skill in the art will recognize the appropriate method of analysis based on factors, such as the skin agent, absorbent article, tape, or area of skin. Listed below is an example of an analytical method that may be used to determine the amount of a skin agent on a tape. The disclosed analytical method is merely for the purpose of illustration, and not to be regarded as limiting the scope of the invention or manner in which it may be practiced.

Analytical Method

Materials

Extraction Solvent Dichloromethane, available from Sigma-Aldrich of St. Louis, Mo. as 27056-3

Stearyl Alcohol Aldrich 25876-8 or Behenyl Alcohol Aldrich 16910-2

1-Hexadecanol Aldrich 25874-1

Dispensing Flask 10 ml

Gas Chromatograph Flame Ionization Detector, Hewlett Packard Model 6890 GC is suitable.

Capillary Column: Chrompack CP Sil-5 CB, 10 meters×0.25 mm×0.12 micron film thickness fused silica capillary 7700

Extraction and Analysis

This method is designed for determining an amount of stearyl alcohol or behenyl alcohol (skin agents) on a TEGADERM tape. In general, the method of analysis may comprise the following steps: 1) stearyl alcohol or behenyl alcohol are extracted from the TEGADERM tape using a suitable solvent; 2) gas chromatographic or other suitable quantitative analytical techniques are then used to determine the level of stearyl alcohol or behenyl alcohol in the extract; 3) amount of stearyl alcohol or behenyl alcohol is calculated as mass per unit area.

Internal Standard/Extraction Solvent

Prepare an internal standard/extraction solvent by accurately weighing 100±2 mg of 1-hexadecanol into a small beaker. Dissolve the 1-hexadecanol in dichloromethane and transfer to a 1 liter volumetric flask. Rinse the beaker 3 more times with dichloromethane transferring each rinse portion to the volumetric flask. Fill the volumetric flask to volume and mix well. This solution will be used to deliver the internal standard and extract the stearyl or behenyl alcohol from a tape. When not being used, this container should be kept tightly capped to prevent evaporation of solvent.

Calibration Standard

Prepare a calibration standard of known concentration by accurately weighing (±0.1 mg) 10±1 mg of stearyl or behenyl alcohol into a 100 ml volumetric flask. Record the weight of stearyl or behenyl alcohol used. Add the internal standard/extraction solvent to the flask and mix to dissolve. Fill to volume and mix well. Make up dilutions: 1 part calibration standard solution with 9 parts internal standard solution and 2 parts calibration standard solution with 9 parts internal standard solution. When not being used, standard containers should be kept tightly capped to prevent evaporation of solvent. These solutions will be used to determine the relative response of the stearyl or behenyl alcohol to the 1-hexadecanol internal standard for calibration of the instrument.

Preparation and Calibration of the Gas Chromatograph (GC)

All equipment should be installed, operated and maintained according to manufacturer's recommendations.

Install the column and check all the gas flows with the column oven at 100° C. and the injection port and detector at operating temperatures. The GC will be operated under the following conditions:

Carrier Gas: Hydrogen (Helium may be used); flow rate 1.5 ml/min

Injection Port: 325° C.; Split vent flow 30 ml/min; Septum purge 2 ml/min; straight through liner with glass wool plug; Merlin microseal.

Injection volume: 2 µl split

FID Detector: 350° C.; set gas flows according to manufacturer suggestions.

Typical gas flows are 400 ml/minute for air, 30 ml/minute for hydrogen and 30 ml/minute for the auxiliary (make up) gas.

Column Oven: 100° C. ramped at 15° C./minute to 325° C.; hold for 10 minutes

Ensure that all connections are tight and leak free. Ignite the detector and allow it to stabilize. Condition the column at 325° C. for 30 minutes. Clean the syringe with dichloromethane as needed. The syringe should also be rinsed with dichloromethane several times after each injection. Make several blank runs with injections of dichloromethane to ensure that a good baseline is obtained and that no extraneous peaks are present in the chromatogram.

Calibrate the instrument using the calibration standard prepared previously. Consult the data system manufacturer's instructions for the proper sequence of operations. Calculations should be performed in a manner similar to that described in CALCULATIONS below in order to provide the desired result.

Sample Analysis Procedure

1) Remove the lid from the sample jar and add 10 ml of the extraction solvent/internal standard solution using the dispensing flask. Replace the cap and swirl the contents to insure that the TEGADERM tape is not adhering to the sides of the jar and is totally submersed in solvent. Repeat for all samples.

2) Allow the samples to sit about 16 hours, overnight or shake samples on an automated shaker for 30 minutes.

3) Swirl the contents of the jar to mix. Using a transfer pipette, transfer an aliquot of the sample extract to a labeled autosampler vial. Cap the vial. Replace jar lid and retain until analyses are complete. Repeat for all samples.

4) Place the vials in the autosampler in random order and start the analyses using the GC conditions described above. The first vial should be a dichloromethane blank. Several "check" standards should be placed (about every 20th sample) through out the run to verify correct operation.

5) At the completion of the run, run software integration program. Check each chromatogram to insure proper analysis. Reanalyze samples as needed.

Calculations

The total micrograms of stearyl alcohol or behenyl alcohol in each sample extract is calculated based on the relative response of the stearyl or behenyl alcohol peak to that of the 1-hexadecanol internal standard. The ratio of the peak areas is multiplied by the relative response factor (determined at time of instrument calibration) and the micrograms of internal standard in the extract to yield the total µg of stearyl or behenyl alcohol in a sample.

Instrument Calibration

Determine the instrumental relative response factor for the stearyl or behenyl alcohol and the internal standard based on the areas of the stearyl or behenyl alcohol and 1-hexadecanol peaks in the calibration standard chromatograms. Develop a calibration curve by plotting the ratioed response factors against the known concentrations of the calibration standards. Use this calibration to determine the parts per million concentrations of the samples using the known peak areas of the samples. The quantity of the stearyl or behenyl alcohol marker is calculated as follows:

$$\text{Total mg SA(BA)} = \text{ppm}_{SA(BA)} \times 0.01 \text{ L IS solution}$$

where

Total mg SA(BA) is total milligrams of stearyl or behenyl alcohol in the sample $\text{ppm}_{SA(BA)}$ ppm is concentration of the stearyl or behenyl alcohol in the sample IS solution is internal standard solution Report amount of lotion transferred in mg/cm² where:

$$\text{Lotion Transferred} = (\text{mg of stearyl or behenyl alcohol in composition})/(\text{tape area})$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for determining an amount of a skin agent transferred from an absorbent article to an area of skin, the method comprising the steps of:
   a. providing an absorbent article including a skin agent;
   b. applying the absorbent article to an area of skin, wherein a means of support secures the absorbent article to the area of skin;
   c. removing the absorbent article from the area of skin;
   d. providing a tape comprising an adhesive layer and a backing material;
   e. releasably attaching the adhesive layer of the tape to the area of skin from which the absorbent article was removed;
   f. removing the tape from the area of skin; and
   g. determining an amount of skin agent present on the adhesive layer of the tape.

2. The method according to claim 1, wherein more than one absorbent article is applied to an area of skin.

3. The method according to claim 1, wherein a baseline determination is attained before the absorbent article is applied to an area of skin.

4. The method according to claim 1, wherein an area of skin is washed prior to application of the absorbent article.

5. The method according to claim 1, wherein more than one type of absorbent article is applied to an area of skin.

6. The method according to claim 1, wherein more than one tape is releasably attached to an area of skin.

7. The method according to claim 6, wherein the outer dimensions of a tape releasably attached to the area of skin are at least partially marked on the area of skin.

8. The method according to claim 1, wherein the adhesive layer of the tape is releasably attached to the area of skin from which the absorbent article was removed by applying pressure in the range of about 0.1 psi to about 3 psi to the backing material of the tape.

9. The method according to claim 1, wherein the skin agent is at least one of stearyl alcohol or behenyl alcohol.

10. The method according to claim 1, wherein the skin agent is at least one of 2-ethylhexyl acrylate, ethyleneglycol dimethacrylate, or 2-ethylhexyl methacrylate.

11. The method according to 1, wherein the area of skin comprises at least one of vulvar skin or mucosal skin.

12. The method according to claim 1, wherein the step of determining an amount of skin agent on at least one tape comprises using a gas chromatograph.

13. A method for determining an amount of a skin agent transferred from an absorbent article to an area of skin, the method comprising the steps of:
   a. providing an absorbent article including a skin agent;
   b. applying the absorbent article to an area of skin, wherein the area of skin is at least one of axilla, popliteal fossa, urogenital area, talus, buccala, auris auricula, palpebra, buccocervical, digitus web, crapus or cubitus and a means of support secures the absorbent article to the area of skin;
   c. removing the absorbent article from the area of skin;
   d. providing a tape, comprising an adhesive layer and a backing material;
   e. releasably attaching the adhesive layer of the tape to the area of skin from which the absorbent article was removed;
   f. removing the tape from the area of skin; and
   g. determining an amount of skin agent present on the adhesive layer of the tape.

14. The method according to claim 13, wherein a baseline determination is attained before the absorbent article is applied to an area of skin.

15. The method according to claim 13, wherein the outer dimensions of a tape releasably attached to the area of skin are at least partially marked on the area of skin.

16. The method according to claim 13, wherein the skin agent is at least one of 2-ethylhexyl acrylate, ethyleneglycol dimethacrylate, or 2-ethylhexyl methacrylate.

17. The method according to claim 13, wherein the skin agent is at least one of stearyl alcohol or behenyl alcohol.

18. The method according to claim 13, wherein the step of determining an amount of skin agent on at least one tape comprises using a gas chromatograph.

* * * * *